United States Patent [19]

Amer

[11] 4,163,382
[45] Aug. 7, 1979

[54] METHOD AND APPARATUS FOR OPTOACOUSTIC SPECTROSCOPY

[75] Inventor: Nabil M. Amer, Berkeley, Calif.

[73] Assignee: The United States of America as represented by the United States Department of Energy, Washington, D.C.

[21] Appl. No.: 901,048

[22] Filed: Apr. 28, 1978

[51] Int. Cl.² .................... G01N 31/00; G01N 21/24
[52] U.S. Cl. ........................................ 73/24; 250/351
[58] Field of Search .................. 73/601, 24; 250/341, 250/343, 351; 356/97, 206

[56] References Cited

U.S. PATENT DOCUMENTS

| | | | |
|---|---|---|---|
| 3,700,890 | 10/1972 | Kruezer | 250/343 |
| 3,820,901 | 6/1974 | Kreuzer | 250/345 |
| 3,938,365 | 2/1976 | Dewey | 73/24 |
| 3,948,345 | 4/1976 | Rosencwaig | 73/24 |

*Primary Examiner*—S. Clement Swisher
*Attorney, Agent, or Firm*—Dean E. Carlson; R. S. Gaither; L. E. Carnahan

[57] ABSTRACT

A method and apparatus that significantly increases the sensitivity and flexibility of laser optoacoustic spectroscopy, with reduced size. With the method, it no longer is necessary to limit the use of laser optoacoustic spectroscopy to species whose absorption must match available laser radiation. Instead, "doping" with a relatively small amount of an optically absorbing gas yields optoacoustic signatures of nonabsorbing materials (gases, liquids, solids, and aerosols), thus significantly increasing the sensitivity and flexibility of optoacoustic spectroscopy. Several applications of this method are demonstated and/or suggested.

10 Claims, 6 Drawing Figures

METHOD AND APPARATUS FOR OPTOACOUSTIC SPECTROSCOPY

BACKGROUND OF THE INVENTION

The invention described herein was made in the course of, or under, Contract No. W-7405-ENG-48 between the University of California and the United States Department of Energy.

The invention relates to optoacoustic spectroscopy, and more particularly, to a method and apparatus which significantly increases the sensitivity and flexibility of laser optoacoustic spectroscopy, and has several applications to analytical instrumentation.

The principal of optoacoustic spectroscopy is known in the art as evidenced by U.S. Pat. Nos. 3,700,890, issued Oct. 24, 1972 and No. 3,820,901 issued June 28, 1974, each in the name of L. B. Kreuzer; L. B. Kreuzer, J. Appl. Phys. 42, 2934 (1971); C. F. Dewey et al, Appl. Phys. Letters 23, 633 (1973); R. D. Kamm, J. Appl. Phys. 47, 3550 (1976); E. Max et al, Opt. Comm. 11, 422 (1974); and C. K. Patel et al, Appl. Phys. Letters 30, 578 (1977). These prior known approaches have been severely limited because some substances have no natural resonant frequency close to an available laser frequency. Thus, a need has existed in the prior art to overcome the above-mentioned limitations of optoacoustic spectroscopy. Furthermore, prior art in the field of optoacoustic detection *never* considered the role of buffer gas and its potential uses.

SUMMARY OF THE INVENTION

The present invention overcomes the above-mentioned limitation on laser optoacoustic spectroscopy by providing a method and apparatus which yields optoacoustic signatures of nonabsorbing materials, thus significantly increasing the sensitivity and flexibility of optoacoustic spectroscopy, which provides reduced size capability. Accordingly, it is no longer necessary to limit the use of laser optoacoustic spectroscopy to species whose absorption must match available laser radiation. According to the method of this invention, "doping" with a relatively small amount of an optically absorbing gas yields optoacoustic signatures of nonabsorbing materials. The sensitivity of the apparatus is sufficient to distinguish small differences in molecular weights, for example, $^{12}CO_2$ and $^{13}CO_2$.

Therefore, it is an object of this invention to provide increased sensitivity and flexibility of laser optoacoustic spectroscopy.

A further object of the invention is to provide a method and apparatus for laser optoacoustic spectroscopy whereby such is no longer limited to species whose absorption must match available laser radiation.

Another object of the invention is to significantly increase the sensitivity and flexibility of optoacoustic spectroscopy by "doping" optically nonabsorbing materials with a relatively small amount of an optically absorbing gas which yield optoacoustic signatures of the nonabsorbing materials.

Another object of the invention is to provide a laser optoacoustic spectroscopy apparatus which has a sensitivity sufficient to distinguish small differences in molecular weights of materials.

Other objects of the invention, not specifically set forth, will become readily apparent from the following description and accompanying drawings.

DETAILED DESCRIPTION OF THE PREFERRED EMBODIMENT

The present invention is directed to an improved optoacoustic spectroscopy method and apparatus which eliminates the prior necessity of limiting the use of laser optoacoustic spectroscopy to species whose absorption must match available laser radiation. It also exploits the role of buffer gases in the optoacoustic detector for use as an analytical tool. The invention basically involves "doping" with a relatively small amount of an optically absorbing gas which yields optoacoustic signatures of nonabsorbing materials, thus significantly increasing the sensitivity and flexibility of optoacoustic spectroscopy, while providing reduced size capability. The invention also involves the dependence of an acoustically resonant optoacoustic signal on the molecular weight, and thermodynamic and transport properties of a buffer gas (defined as the optically nonabsorbing gaseous component in optoacoustic detectors) in optoacoustic spectroscopy. It has been found that careful selection of the buffer gases can significantly increase the sensitivity and flexibility of optoacoustic spectroscopy. It has also been demonstrated that such thermodynamic quantities as $\gamma(\equiv C_p/C_v)$ and sound velocity can be measured readily and accurately.

In principle, the molecular weight and thermodynamic and transport properties of a buffer gas have a significant impact upon the optoacoustic signal, and the present invention has verified that the energy transfer between the absorbing species and the buffer gas plays an important role in optoacoustic detection. The dependence of the optoacoustic signal has been investigated to verify the invention on the following physical properties of the buffer gas: molecular weight and isotopic effects, heat capacity, thermal conductivity, and viscosity with respect to acoustically resonant detectors.

The following series of noble, diatomic, and polyatomic gases were investigated in verifying the invention: Ne, Ar, Kr, Xe, $N_2$, CO, $N_2O$, $^{12}CO_2$, $^{13}CO_2$, and $SF_6$. The optically absorbing molecule utilized in the tests was $CH_4$ whose $\nu_3$ absorption band lies conveniently in near coincidence with the 3.39 $\mu$m output of He-Ne lasers.

Figure 1:
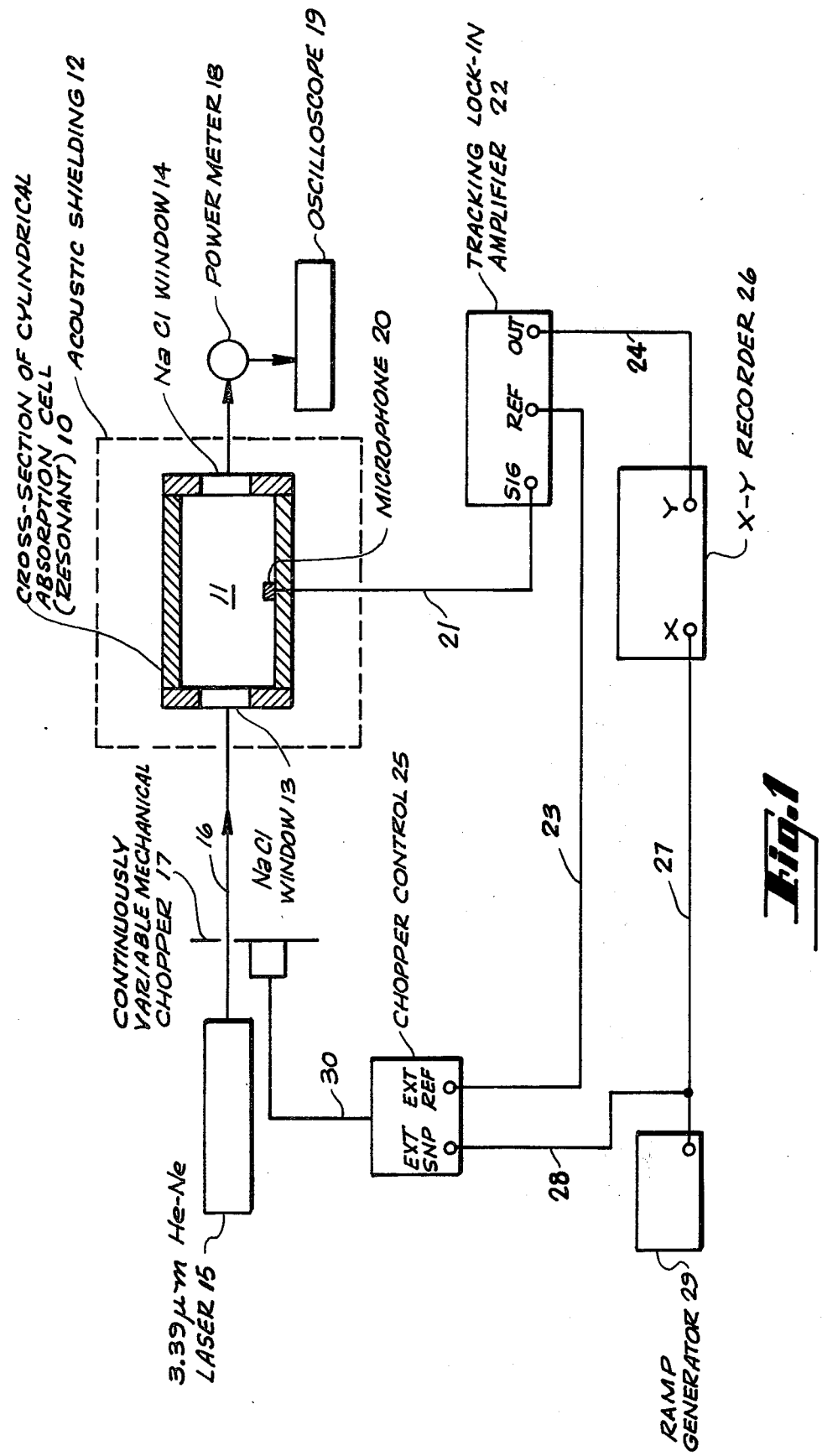
FIG. 1 is a schematic diagram of an embodiment of the apparatus of the invention.

FIG. 1 illustrates an embodiment of the apparatus which consists of an acoustically resonant cylindrical absorption cell 10 defining a chamber or cavity 11 located within an acoustic shielding 12 having windows 13 and 14 positioned in opposite ends thereof, a laser 15 directing a light beam 16, via a continuously variable mechanical chopper 17, through window 13, cavity 11 and window 14, and onto a power meter 18, the output of which is directed to an oscilloscope 19. A microphone 20 is mounted in cavity 11 of cell 10 and is connected via lead 21 to a tracking lock-in amplifier 22 connected via leads 23 and 24, respectively, to a chopper control 25 and an X-Y recorder 26, recorder 26 being connected via leads 27 and 28 to a ramp generator 29 and to chopper control 25, which in turn is operatively connected to chopper 17 by lead 30.

By way of example, the optoacoustic cell 10 is constructed of a brass cylinder 10.8 cm in length and in diameter, with windows 13 and 14 being NaCl flats, and chamber 11 containing a small quantity (0.9%) of gas such as methane ($CH_4$) whose resonant frequency is near to a particular light frequency from laser 15, which is an He-Ne laser having a 3.39 $\mu$m beam 16. The cavity or chamber 11 also contains a buffer gas, such as the noble, diatomic, and polyatomic gases listed above. The microphone 20, may, for example, be a Knowles Electronics model BT-1759 miniature electret microphone (sensitivity of 10 mV/Pa) with a built-in FET preamplifier and is attached to the inner wall of cell 10 midway between the cell ends. The choice of a miniature microphone is particularly advantageous since it can be readily incorporated in the resonant cavity without significantly degrading the Q of the resonances. Care was taken to insure mechanical and acoustical isolation of the detector. The noise level, which is electrical in origin, was found to be $\sim 90$nV/$Hz^{1/2}$ with the above-embodied apparatus. The gas temperature was monitored throughout the test operation.

Basically, in operation of the FIG. 1 embodiment, with the cavity 11 containing the selected buffer gas and absorbing gas, $CH_4$, for example, the laser light 15 is pulsed by mechanical chopper 17, and the energy pulses absorbed by the methane molecules are communicated to the buffer gas, resulting in pulsed acoustic waves. By varying the chopper rate, the cavity can become acoustically resonant to the buffer gas, making possible measurements of the velocity of sound in the gas, the ratio of its specific heat at constant pressure to that at constant volume, its heat conductivity, viscosity, and molecular weight. The sensitivity of the apparatus is sufficient to distinguish small differences in molecular weights, for example, $^{12}CO_2$ and $^{13}CO_2$.

In the case of a binary gas mixture, for a cylindrical cell the acoustic resonant frequencies are given by $$f_{mnp} = \frac{\bar{v}_s}{2}\left[\left(\frac{\alpha_{mn}}{r}\right)^2 + \left(\frac{p}{l}\right)^2\right]^{\frac{1}{2}} \quad (1)$$

where $f_{mnp}$ is the frequency at which the acoustical modes occur. The eigenvalues m,n, and p refer to radial, azimuthal, and longitudinal modes, respectively; r is the radius and l the length of the cavity, $\alpha_{mn}$ is the $m^{th}$ zero of the derivative of the Bessel function $dJ_n(\pi\infty)/d\infty$, and $\bar{v}_s$ is the sound velocity in a mixture of ideal gases and is given by $\bar{v}_s = (\bar{\gamma}RT/\bar{M})^{1/2}$ where R is the ideal gas constant. The effective specific heat ratio $\bar{\gamma}$ and the average molecular weight $\bar{M}$ for the mixture was determined from $$\bar{\gamma} = \frac{x\, C_p^b + (1-x)\, C_p^a}{x\, C_v^b + (1-x)\, C_v^a}\; ; \; \bar{M} = x\, M^b + (1-x)\, M^a$$

where $C_p^b$, $C_v^b$, $C_p^a$, and $C_v^a$ are the heat capacities of the buffer and absorbing gases, respectively; $M^b$ and $M^a$ are their molecular weights; and x is the fractional concentration of the buffer gas.

From Eq. (1) it can be seen that the acoustic resonant frequencies are partially determined by the combined properties of the buffer and absorbing gases. In the case herein described, since $x > (1-x)$, the acoustical behavior of the cell will largely be determined by $\gamma$ and M of the buffer gas.

Figure 2:
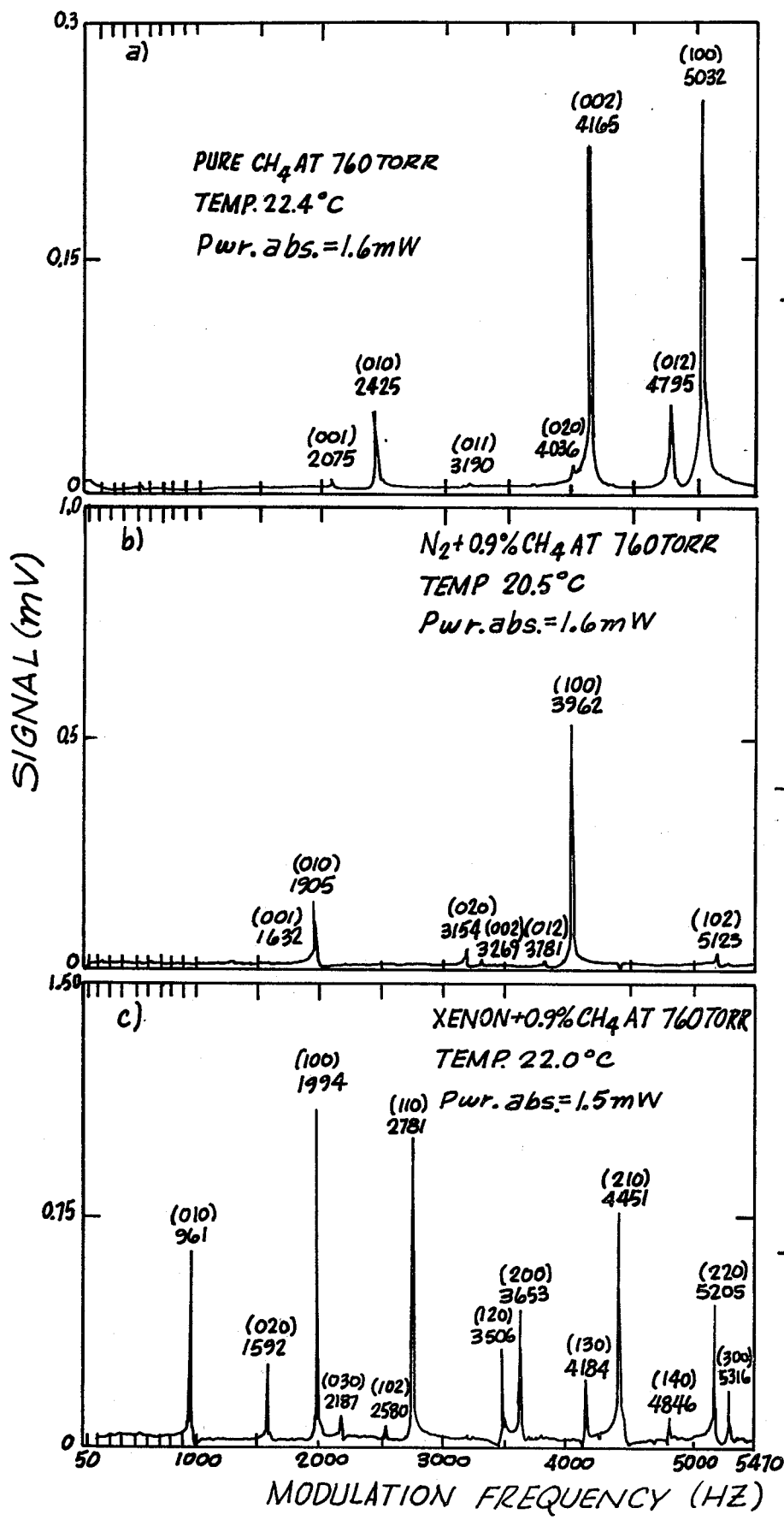
FIGS. 2a to 2c graphically illustrate typical acoustically resonant optoacoustic spectra resulting from the invention.

In FIGS. 2a, 2b, and 2c are shown typical acoustical excitation spectra for pure $CH_4$, 0.9% $CH_4$ in $N_2$, and 0.9% $CH_4$ in Xe, respectively, and in Table I is summarized the results.

TABLE I

| Buffer Gas[b] | $f_{100}$(Hz)[c] | $Q_{exp}$[d] | $Q_{exp}/Q_{cal}$ | S/N |
|---|---|---|---|---|
| Ne | 5074 | 554 | 0.56 | 3800 |
| Ar | 3619 | 694 | 0.62 | 6300 |
| Kr | 2495 | 832 | 0.86 | 11000 |
| Xe | 1995 | 903 | 0.95 | 14000 |
| CO | 3967 | 929 | 0.63 | 4900 |
| $N_2$ | 3966 | 1030 | 0.71 | 5700 |
| $^{12}CO_2$ | 3030 | 250 | 0.16 | 1400 |
| $^{13}CO_2$ | 2994 | 270 | — | 1700 |
| $N_2O$ | 3009 | 673 | 0.43 | 3300 |
| $SF_6$ | 1522 | 1220 | 0.99 | 5500 |

[a]$C_p$, $\kappa$ and $\eta$ were obtained from K. Raznjevic, Handbook of Thermodynamic Tables and Charts; JANAF Thermodynamic Tables, NBS 37, 1971; and Trans. Farad. Soc. 53, 877 (1957); $f_{100}$, $Q_{exp}$, $Q_{exp}/Q_{cal}$, and S/N for $CH_4$, without buffer gas, are 5033Hz, 500, 0.24, and 2800, respectively.
[b]Spectroscopic Grade.
[c]Typical uncertainty 1 Hz; $f_{100}$ values agree to better than 0.8% with those calculated from Eq. (1).
[d]Q measured at half-power; typical uncertainty < 5%

The agreement between the observed resonance frequencies and those calculated from Eq. (1) is excellent. Furthermore, the experimentally deduced velocity of sound for the different gases tested agrees to within $\leq 0.8\%$ of the calculated values. The discrepancy is attributable to uncertainties in the temperature and dimensions of the cell. As predicted, when the molecular weight of the buffer gas is increased, the resonance frequencies of the cavity shift to lower values.

In Table I is listed the signal-to-noise ratio (S/N) as well as the experimentally and theoretically derived quality factor Q for different buffer gases. It can be seen that Xe enhances significantly the amplitude of the optoacoustic signal and yields the highest S/N observed. The largest experimental Q obtained was that of $SF_6$, with $CO_2$ proving to be the most dissipative.

It should be noted that the amplitude of the optoacoustic signal is a function of: (1) the heat capacity of the mixture, (2) the laser power absorbed, (3) the modulation frequency, (4) the vibrational relaxation times of $CH_4$, and (5) damping effects of the buffer gas. The first four contribute to the power going into the sound wave, and the last mechanism determines the Q of the resonances.

Assuming that boundary layer losses are the dominant dissipation mechanism, a theoretical Q can be obtained from $$\frac{1}{Q} = \frac{1}{l}\left[d_v + (\bar{\gamma} - 1)\, d_h\left(1 + \frac{l}{r}\right)\right] \quad (2)$$

where the viscous boundary layer thickness $d_v = (2\eta/\rho\omega)^{1/2}$, the thermal boundary layer thickness $d_h = (2\kappa/\rho C_p \omega)^{1/2}$, $\eta$ is the viscosity, $\kappa$ the thermal conductivity, $\rho$ the density of the gas mixture, and $\omega$ is the frequency.

Although it is not the purpose here to fully account for the observed Q's, the ratio $Q_{exp}/Q_{cal}$ is an indication of the relative significance of different energy dissipating mechanisms in the optoacoustic cavity. A value of unity for this ratio indicates that the viscous and thermal dissipations at the cell wall are the sole sources for sound energy loss. When $Q_{exp}/Q_{cal} < 1$, additional dissipating mechanisms have to be invoked in order to explain this discrepancy. For in the case of diatomic and polyatomic molecules, the energy losses due to shear friction and thermal diffusion are only part of the sound wave attenuating mechanism. One must, in addition, take into account the irreversible energy transfer from the sound wave to the internal degrees of freedom of the molecule; as a consequence, one would expect the characteristic relaxation times governing those transfer rates to affect the Q. Clearly, complete knowledge of the bulk relaxation times of the mixtures involved is necessary for understanding the role of molecular relaxation times in determining the Q. As to other loss mechanisms normally considered, e.g., Stokes-Kirchhoff losses, reflection, motion of microphone diaphragm, they can be shown to have negligible effect; while the Xe and $SF_6$ data limit the scattering contribution to <5%.

Figure 3:
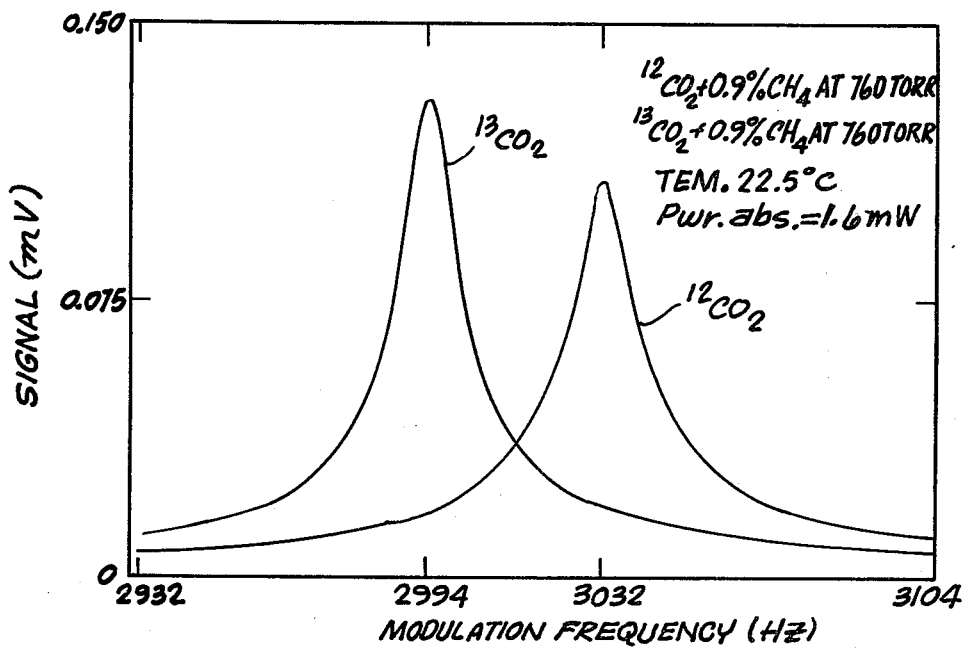
FIG. 3 graphically shows the first radial mode of the isotopically substituted pair $^{12}CO_2$ and $^{13}CO_2$.

Typical resonant optoacoustic spectra contain three useful quantities: the frequency, the Q, and the amplitude of the signal. An illustration of their utility is given in the following two examples:

(1) It is of interest to investigate the ability of optoacoustic spectroscopy to mass-resolve two isotopes of the same molecular species. FIG. 3 shows the acoustic signatures for the first radial mode of $^{12}C\ ^{16}O_2$ and $^{13}C\ ^{16}O_2$. As expected, due to the mass difference, the frequency of the (100) mode shifts from 3032 Hz to a lower value of 2994 Hz, which is in complete agreement with the theoretical prediction of Eq. (1). In this example, the composition of the absorbing and buffer gases by volume consisted of 0.9% and 99.1%, respectively.

Figure 4:
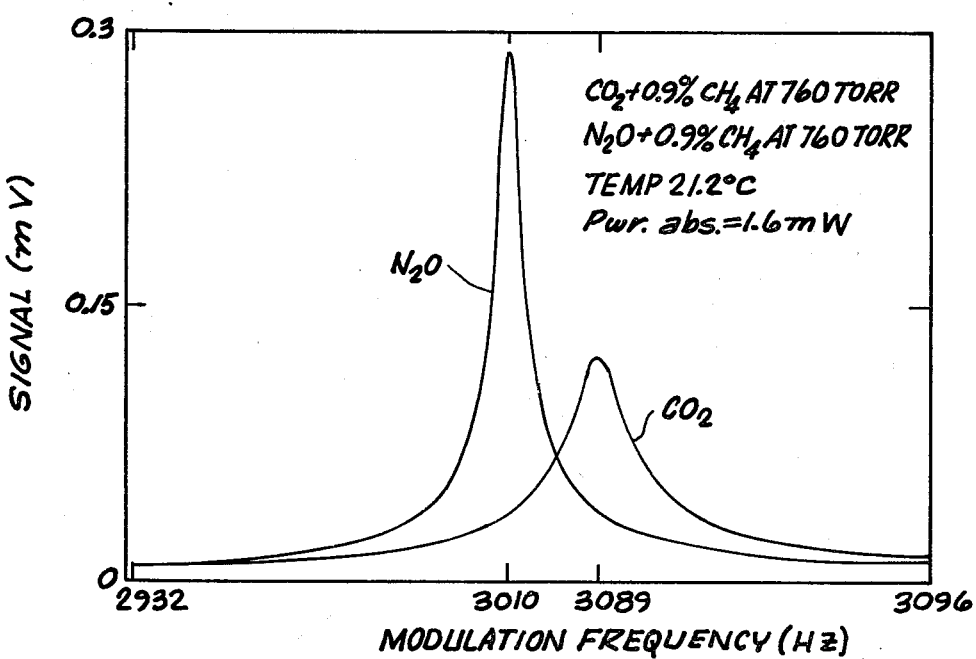
FIG. 4 graphically shows the first radial mode of $^{12}CO_2$ and $N_2O$.

(2) To verify the sensitivity of the approach to differences in $\gamma$ when the molecular weight is very nearly identical, the (100) resonance frequency for $N_2O$ and $^{12}CO_2$ whose molecular weights are 44.013 and 44.010, and whose $\gamma$'s are 1.301 and 1.287, respectively, were determined. From Eq. (1) the first radial mode for $N_2O$ and $^{12}CO_2$ should occur at 3009 and 3030 Hz, respectively. In FIG. 4 is presented the experimental spectra which agree very well with the predicted values and which correspond to a difference of only 1.8 m/sec. in the sound velocity in the two gases. Here the percentages by volume of the absorbing and buffer gases were 0.9% and 99.1%, respectively.

The practical implications of the results are manifold. First, with respect to extending the flexibility and sensitivity of optoacoustic spectroscopy: it has been shown that it is no longer necessary to limit the applicability of laser optoacoustic spectroscopy to species whose absorption must match available laser radiation. Instead, "doping" with a relatively small amount of an optically absorbing gas yields optoacoustic signatures of nonabsorbing materials. It has also been demonstrated that, for a fixed cavity dimension, the molecular weight of the buffer gas can serve as a means of shifting the frequency of the acoustical resonances to any region of interest for the purpose of optimizing S/N; furthermore, irrespective of the frequency dependence on molecular weight, the use of such buffer gases as Xe enhances the sensitivity of optoacoustic detection. A consequence of both results is that, in the case where resonant optoacoustic detection is desirable, it now becomes possible to construct *miniature* resonance optoacoustic detectors by employing the appropriate high molecular weight buffer gas. Such a compact, room temperature detector can be of use in, for example, conventional and Fourier infrared spectroscopy and in gas chromatography-infrared analyzers.

Second, the findings point to the potential of this technique as a versatile analytical tool for "coarse" mass spectroscopy and isotope analysis, for gas analysis, and for monitoring chemical reactions via changes in heat capacity and sound velocity.

Finally, it has been shown the quantities such as $\gamma$ and $v_s$ can now be measured readily by optoacoustic spectroscopy. In fact, it is believed that this is the first experimentally deduced values for $\gamma$ for $v_s$ of $^{13}CO_2$ at 22.5° C. The values are 1.279 and 264.4 m/sec, respectively. It may also be possible to determine virial coefficients of gases by measuring the pressure dependence of sound velocity in high pressure optoacoustic cells.

Accordingly, the invention has a variety of applications, such as in a coarse mass spectrometer, gas analyzer, detector for conventional and Fourier infrared (and visible) spectrometers, detector for gas-chromatograph-/infrared analyzers, detector for mass-spectrometer/infrared analyzers, miniature acoustically-resonant optoacoustic detector, and finally chemical reaction monitor.

It has thus been shown that the present invention greatly advances the state of the optoacoustic spectroscopy art by providing a method and apparatus which produces increased sensitivity, flexibility, and reduced size.

While particular parameters, materials, and apparatus have been illustrated and/or described, modifications and changes will become apparent to those skilled in the art, and it is intended to cover in the appended claims all such modifications and changes as come within the spirit and scope of the invention.

What is claimed is:

1. An optoacoustic spectroscopy method comprising the steps of containing a gaseous mixture of an optically nonabsorbing gas whose properties are to be determined and an optically absorbing gas, directing pulsed light through the thus contained gaseous mixture such that at least a portion of the energy of the pulsed light is absorbed by the optically absorbing gaseous component of the mixture and communicated to the nonabsorbing gaseous component of the mixture resulting in pulsed acoustic waves, and detecting and measuring the thus produced acoustic waves, such that the velocity of sound in the optically nonabsorbing gas component, the ratio of its specific heat at constant pressure to that at constant volume, its heat conductivity, viscosity, and molecular weight can be determined.

2. The method defined in claim 1, additionally including producing the pulsed light by a laser, the output of which is directed through a variable rate chopper.

3. The method defined in claim 1, additionally including the step of forming the gaseous mixture consisting of the optically absorbing gas composed of $CH_4$ and the optically nonabsorbing gas composed of at least one gas selected from the group consisting of Ne, Ar, Kr, Xe, $N_2$, CO, $N_2O$, $^{12}CO_2$, $^{13}CO_2$, and $SF_6$.

4. The method defined in claim 3, additionally including the step of producing the pulsed light from an He-Ne laser having a 3.39 $\mu$m output.

5. The method defined in claim 1, additionally including the step of varying the pulse rate of the pulsed light such that a cavity containing the gaseous mixture becomes acoustically resonant to the optically nonabsorbing gas component of the mixture.

6. An optoacoustic spectroscopy apparatus comprising an absorption cell defining a cavity therein for containing a mixture of an optically absorbing gas and an optically nonabsorbing gas whose properties are to be determined, said cell being provided with windows at opposite ends thereof, a light producing means for directing light through said cell, variable rate chopper means located intermediate said cell and said light producing means for producing pulses of light, a microphone means operatively secured in said cavity of said cell having an output operatively connected to a tracking lock-in amplifier, said amplifier being operatively connected to a chopper control means and to an X-Y recorder means, said X-Y recorder means being operatively connected to a ramp generator and said chopper control means, said chopper control means being operatively connected to said variable rate chopper means.

7. The apparatus defined in claim 6, additionally including a power meter means positioned to receive light passing through said windows of said cell, and oscilloscope means positioned to receive an output signal from said power meter means.

8. The apparatus defined in claim 6, wherein said light producing means is a 3.39 $\mu$m He-Ne laser, and wherein said cavity contains a quantity of a gaseous mixture composed of $CH_4$ gas and at least one gas selected from the group consisting of Ne, Ar, Kr, Xe, $N_2$, CO, $N_2O$, $^{12}CO_2$, $^{13}CO_2$, and $SF_6$.

9. The apparatus defined in claim 6, wherein said light producing means is a laser, and wherein said cavity is provided with a mixture of optically absorbing gas and an optically nonabsorbing gas whose properties are to be determined.

10. The apparatus defined in claim 6, wherein said cavity is cylindrically configured so as to become resonant, and wherein said windows are composed of NaCl.

* * * * *